US006964076B2

(12) United States Patent
Zhuan

(10) Patent No.: US 6,964,076 B2
(45) Date of Patent: *Nov. 15, 2005

(54) ELECTRIC TOOTHBRUSH

(76) Inventor: Qingping Zhuan, 5980 Whitehorn Avenue, Unit 110, Mississauga, Ontario (CA) L5V 2Y5

( * ) Notice: Subject to any disclaimer, the term of this patent is extended or adjusted under 35 U.S.C. 154(b) by 0 days.

This patent is subject to a terminal disclaimer.

(21) Appl. No.: 10/822,857

(22) Filed: Apr. 13, 2004

(65) Prior Publication Data

US 2004/0226121 A1      Nov. 18, 2004

Related U.S. Application Data

(63) Continuation of application No. 09/892,861, filed on Jun. 28, 2001, now Pat. No. 6,721,986.

(51) Int. Cl.$^7$ .......................... A61C 3/03; F16H 21/16; A46B 13/00
(52) U.S. Cl. .................. 15/22.2; 15/22.1; 433/118; 433/122; 433/131; 74/25
(58) Field of Search .................. 15/21.1, 22.1, 15/22.2, 22.4, 28

(56) References Cited

U.S. PATENT DOCUMENTS

| | | | |
|---|---|---|---|
| 3,577,579 A | * | 5/1971 | Duve et al. ............... 15/22.1 |
| 5,353,460 A | * | 10/1994 | Bauman ................. 15/22.1 |
| 5,493,747 A | | 2/1996 | Inakagata et al. |
| 5,504,958 A | | 4/1996 | Herzog |
| 5,504,959 A | | 4/1996 | Yukawa et al. |
| 5,504,960 A | | 4/1996 | Hommann |
| 5,504,961 A | | 4/1996 | Yang |
| 5,524,312 A | | 6/1996 | Tan et al. |
| 5,561,881 A | | 10/1996 | Klinger et al. |
| D375,204 S | | 11/1996 | Okada |
| 5,577,285 A | | 11/1996 | Drossler |
| 5,590,434 A | | 1/1997 | Imai |
| 5,617,603 A | | 4/1997 | Mei |
| 5,651,157 A | | 7/1997 | Hahn |
| 5,652,990 A | | 8/1997 | Driesen et al. |
| 5,697,117 A | | 12/1997 | Craft |
| D388,958 S | | 1/1998 | Hartwein |
| 5,732,432 A | | 3/1998 | Hui |

(Continued)

FOREIGN PATENT DOCUMENTS

DE            3544256 A1  *  6/1987

OTHER PUBLICATIONS

English translation of DE 3544256 A1 to Ullrich, Volker; Jun. 1987.*

*Primary Examiner*—John Kim
*Assistant Examiner*—Laura C Cole
(74) *Attorney, Agent, or Firm*—Bereskin & Parr

(57) ABSTRACT

In one aspect, the present invention is directed to an electric toothbrush. The toothbrush includes a housing, an electric motor, a first transmission and a second transmission. The electric motor is connected to the housing has a motor output member for rotation about a motor output axis. The first transmission is connected to the housing, and converts rotational movement from the motor output member into rotational reciprocating movement at a first average angular speed. The second transmission is linked to the first transmission, and converts rotational reciprocating movement from the first transmission into rotational reciprocating movement at a second average angular speed about a second transmission output axis that is parallel to the motor output axis. The second transmission drives an output member to reciprocate at the second average angular speed about the second transmission output axis. A brush head is removably connectable to the output member.

6 Claims, 4 Drawing Sheets

U.S. PATENT DOCUMENTS

| | | |
|---|---|---|
| 5,732,433 A | 3/1998 | Gocking et al. |
| D394,751 S | 6/1998 | Eguchi et al. |
| 5,784,742 A | 7/1998 | Giuliani et al. |
| 5,784,743 A | 7/1998 | Shek |
| 5,794,296 A | 8/1998 | Wong |
| 5,822,821 A | 10/1998 | Sham |
| RE35,941 E | 11/1998 | Stansbury, Jr. |
| 5,842,244 A | 12/1998 | Hilfinger et al. |
| 5,842,245 A | 12/1998 | Pai |
| 5,850,655 A | 12/1998 | Gocking et al. |
| 5,862,558 A | 1/1999 | Hilfinger et al. |
| 5,862,559 A | 1/1999 | Hunter |
| 5,867,856 A | 2/1999 | Herzog |
| 5,934,908 A | 8/1999 | Woog et al. |
| 5,943,723 A | 8/1999 | Hilfinger et al. |
| 5,974,613 A | 11/1999 | Herzog |
| 5,974,615 A | 11/1999 | Schwarz-Hartmann et al. |
| 5,987,681 A | 11/1999 | Hahn et al. |
| 6,000,083 A | 12/1999 | Blaustein et al. |
| 6,021,538 A | 2/2000 | Kressner et al. |
| 6,092,252 A | 7/2000 | Fischer et al. |
| 6,138,310 A | 10/2000 | Porper et al. |
| 6,178,579 B1 | 1/2001 | Blaustein et al. |
| 6,230,354 B1 | 5/2001 | Sproat |
| 6,721,986 B2 * | 4/2004 | Zhuan ........................ 15/22.1 |

* cited by examiner

US 6,964,076 B2

ELECTRIC TOOTHBRUSH

This application is a continuation of application Ser. No. 09/892,861 filed Jun. 28, 2001, now U.S. Pat. No. 6,721,986 the entirety of which is hereby incorporated by reference.

FIELD OF THE INVENTION

The present invention relates to an electric toothbrush.

BACKGROUND OF THE INVENTION

Electric toothbrushes utilize an electric motor to drive a brush head to provide a brushing action for cleaning teeth. One such toothbrush is disclosed by Sham in U.S. Pat. No. 5,822,821. Sham discloses an electric toothbrush having a motor, which drives a driven gear. The driven gear drives a crank member. The crank member, in turn drives a reciprocating rocker arm. The rocker arm, in turn, drives a brush head. The rate of rotation of the driven gear in the device determines the frequency of reciprocation of the brush head, while the length and shape of the crank member determine the angular sweep and the average angular speed of the brush head.

SUMMARY OF THE INVENTION

The present invention is directed to an electric toothbrush, comprising a housing, an electric motor, a first transmission and a second transmission. The electric motor is linked to the housing, and drives a motor output member for rotation about a motor output axis. The first transmission is linked to the motor output member and converts rotational movement from the motor output member into rotational reciprocating movement at a first average angular speed and along a first angular sweep. The second transmission is linked to the first transmission and converts rotational reciprocating movement from the first transmission into rotational reciprocating movement at a second average angular speed about a second transmission output axis that is parallel to the first axis, and along a second angular sweep. The second transmission drives an output member to reciprocate at the second average angular speed about the second transmission output axis, and along the second angular sweep. The second transmission can include first and second gear members. The first gear member can include a section of an internal gear connected to the first transmission. The second gear member is drivenly connected to the first gear member and comprises a spur gear. The output member can include a removably attachable brush head.

BRIEF DESCRIPTION OF THE DRAWINGS

The present invention will now be described by way of example only with reference to the attached drawings in which.

DETAILED DESCRIPTION OF THE INVENTION

Figure 1:
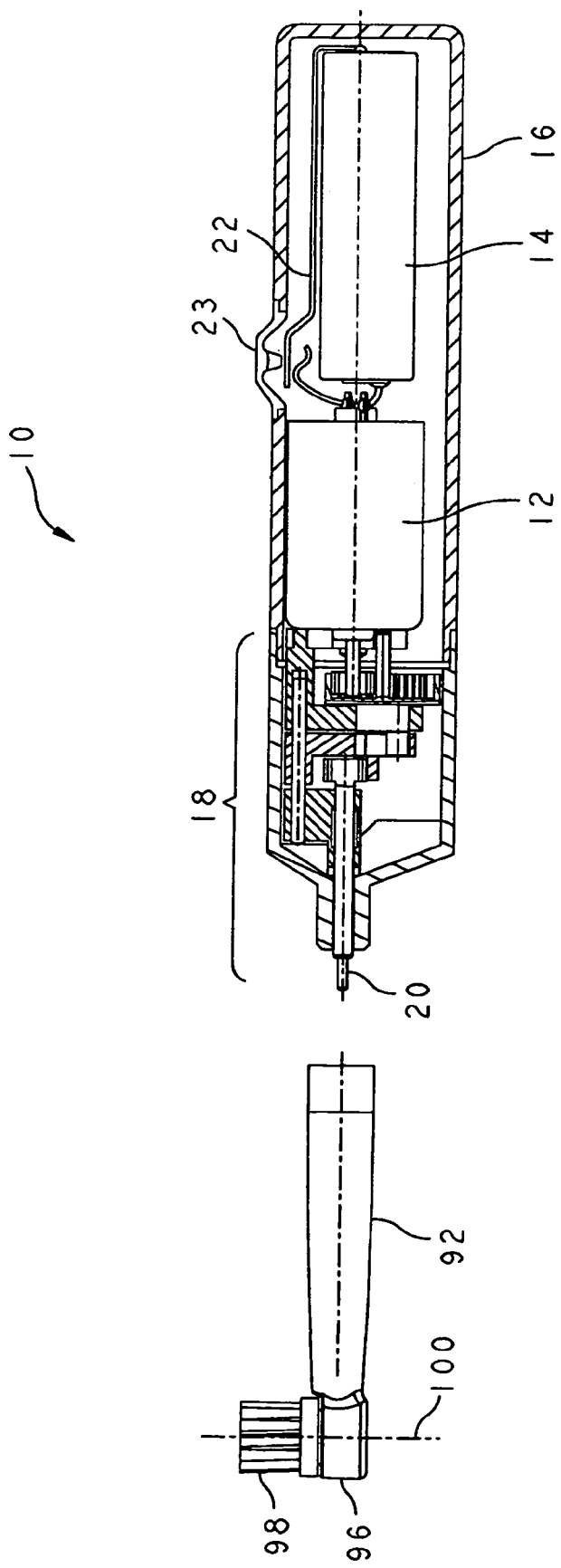
FIG. 1 is a cutaway side elevation view of an electric toothbrush in accordance with a preferred embodiment of the present invention.

Reference is first made to FIG. 1, which illustrates an electric toothbrush 10 in accordance with a first preferred embodiment of the present invention. Toothbrush 10 provides a reciprocating, back-and-forth brushing action, with a large angular sweep during each stroke.

Toothbrush 10 comprises motor 12, a power source 14, a housing 16, a drive mechanism 18 and an output member 20. Motor 12 drives drive mechanism 18 and, in turn, output member 20. Motor 12 can be any suitable compact electric motor. Power source 14 is used to supply power to motor 12. Power source 14 is preferably a battery, as shown in FIG. 1, but may alternately be a connection to an external power source, such as, for example, an electric wire and plug for connection to a standard 120 VAC source. A control line 22 connects power source 14 to motor 12. Control line 22 schematically represents a suitable electrical connection between power source 14 and motor 12. A switch 23 is included on the housing, and connects to control line 22 to start and stop motor 12.

Housing 16 surrounds motor 12, power source 14 and drive mechanism 18, and can provide a base for mounting the components. Housing 16 is made from a suitable, water impermeable plastic to prevent water from damaging the internal electrical components and to prevent a user from potential harm during use. Alternatively, housing 16 can be made from other suitable, water impermeable materials, such as a suitable metal, or from a composite of materials such as metal and plastic.

Figure 2A:
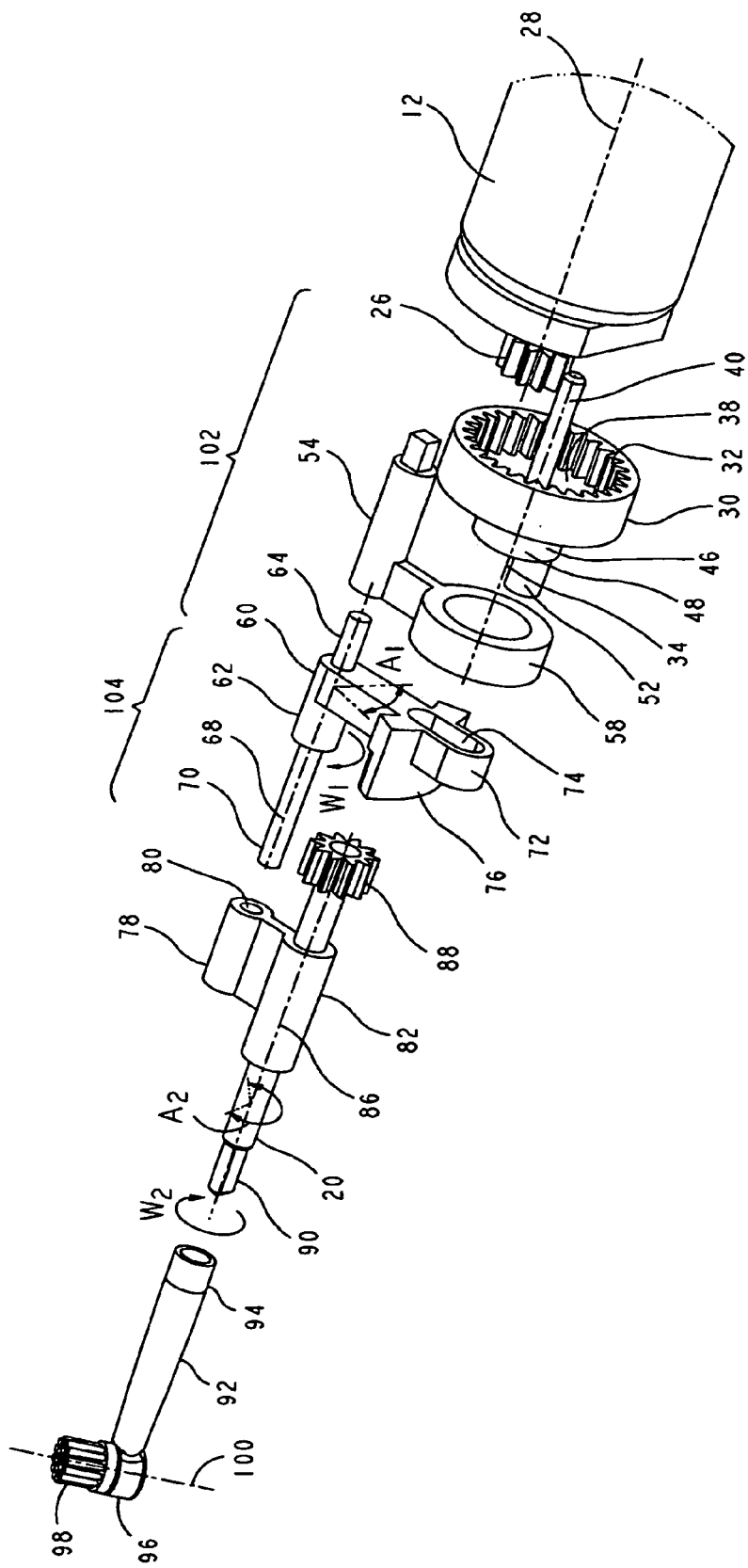
FIG. 2a is an exploded perspective view of a portion on the electric toothbrush shown in FIG. 1.
Figure 2B:
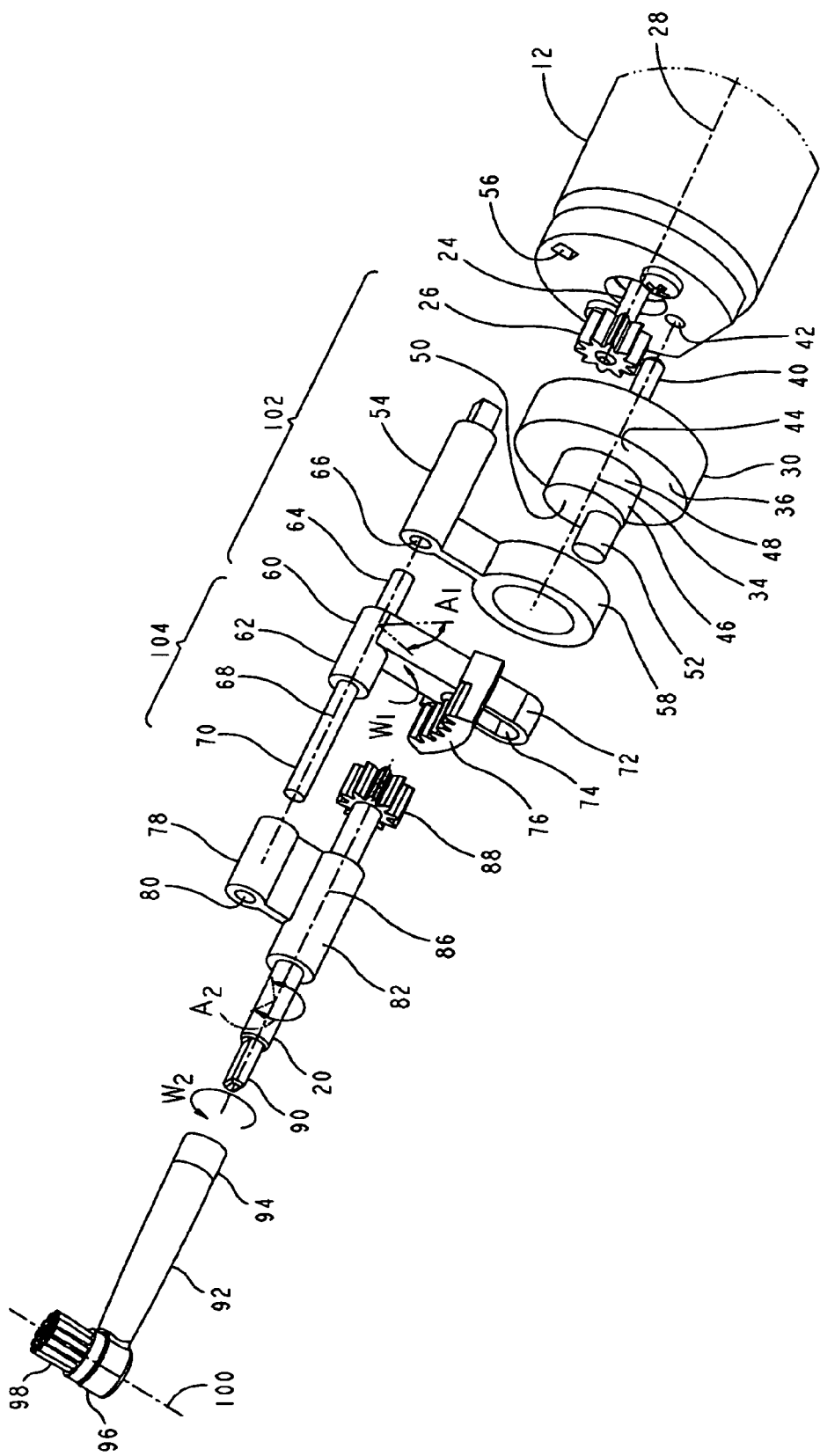
FIG. 2b is another exploded perspective view of a portion on the electric toothbrush shown in FIG. 1.

Reference is now made to FIGS. 2a and 2b, which illustrate drive mechanism 18. Motor 12 drives an output shaft 24, on which is mounted a pinion gear 26. Output shaft 24 and pinion gear 26 rotate about a first axis 28, which is the motor output axis. Pinion gear 26 drives the rotation of a first member 30.

First member 30 includes an internal gear 32 and rotates about a second axis 34. At the forward end of internal gear 32 is a central disc 36. Disc 36 has a first face 38 (see FIG. 2a) from which a central shaft 40 extends. The distal end of shaft 40 rotates within a hole 42, for the embodiment illustrated, the casing of motor 12. Disc 36 has a second face 44 from which a bearing portion 46 extends. Bearing portion 46 has a bearing surface 48 and an end face 50, from which an orbiting member 52 extends. Orbiting member 52 is positioned towards the outside edge of end face 50, so that as first member 30 rotates about axis 34, orbiting member 52 orbits about axis 34.

A second member 54 is attached to a square recess 56, for the embodiment illustrated, the casing of motor 12, and to bearing portion 46 of first member 30. Second member 54 includes a bearing hoop 58 for supporting the rotation of bearing portion 46 therein. Bearing portion 46 and bearing hoop 58 have substantially the same width. Orbiting member 52, which is mounted on bearing portion 46, extends past the forward face of bearing hoop 58.

A third member 60 includes a body 62. A first shaft portion 64 extends rearwardly from body 62 and is received in a hole 66 in the second member 54 for rotation therein about a third axis 68. A second shaft portion 70 extends forwardly from body 62. The third member 60 includes a slotted arm 72, which extends radially from body 62. Arm 72 defines a slot 74 that receives and engages orbiting member 52. As orbiting member 52 orbits about axis 34, the orbiting motion causes arm 72 to reciprocate rotationally about axis 68. In use, arm 72 reciprocates through an angular sweep $A_1$ at an average angular speed $W_1$.

As arm 72 reciprocates, it will have a range of angular speeds, ranging from a speed of zero at the ends of the reciprocation to a maximum speed in the middle of the reciprocation. Since the instantaneous speed of arm 72 varies depending on its position, the average angular speed is used for the purposes of this disclosure.

Extending forwardly from arm 72 is a gear member 76 which is a section of an internal gear. A fourth member 78 includes a receiving hole 80 for receiving shaft portion 70 so that shaft portion 70 can rotate therein. Fourth member 78 includes a bearing portion 82, in which is mounted output member 20. Output member 20 rotates within bearing portion 82 about a fourth axis 86, and includes at its rear end a spur gear member 88 which is driven about axis 86, through an angular sweep $A_2$ at an average angular speed $W_2$ by gear member 76 on third member 60. Gear member 88 has a smaller radius than gear member 76. The average angular speed $W_2$ and the angular sweep $A_2$ of gear member 88 are larger than the average angular speed $W_1$ and the angular sweep $A_1$ of gear member 76 in inverse proportion to the ratio of their radii. Thus, a relatively large angular sweep and a high rotational speed are achieved in output member 20 while keeping the angular sweep and the rotational speed relatively low in the arm 72. As shown in FIG. 1, the forward portion of output member 20 protrudes through a hole in housing 16, and includes a square end portion 90, for the mounting of a brush head member 92 thereon.

Referring back to FIGS. 2a and 2b, brush head member 92 includes a mounting portion 94 for receiving end portion 90 of output member 20. Head member 92 includes a brush head 96 that comprises an arrangement of bristles 98. Bristles 98 extend along an axis 100, that can be perpendicular from the forward end of head member 92 and from fourth axis 86 as shown. Alternately, bristles 98 can extend along an axis that is at some other angle from the forward end of head member 92 and from axis 86. In use, brush head 96 reciprocates through angular sweep $A_2$ at an average angular speed $W_2$, about fourth axis 86. Angular sweep $A_2$ is different than angular sweep $A_1$ and in the embodiment shown, angular sweep $A_2$ is larger than angular sweep $A_1$. Similarly, the average angular speed $W_2$ is different than, and in the embodiment shown, larger than the average angular speed $W_1$. The sweeping action of the brush head member 92 along angular sweep $A_2$ and at average angular speed $W_2$ simulates the back-and-forth brushing action that occurs when a person brushes their teeth with a manual toothbrush. Brush head member 92 is removable for replacement when brush head 96 becomes worn or broken.

First member 30, second member 54, and third member 60, not including gear member 76, make up a first transmission, shown generally at 102. Transmission 102 transfers rotational motion about axis 28, from output shaft 24 of motor 12 into rotational reciprocating motion of slotted arm 72 through angular sweep $A_1$ at average angular speed $W_1$. Member 60, not including gear member 76 is the output member for the first transmission 102. Thus axis 68 is the output member axis for the first transmission 102.

Gear members 76 and 88 make up a second transmission, shown generally at 104. Transmission 104 transfers the rotational reciprocating motion of slotted arm 72 into rotational reciprocating motion of output member 20 through angular sweep $A_2$ at average angular speed $W_2$, about axis 86. Member 88 is the output member for the second transmission 104. Thus axis 86 is the output member axis for the second transmission 104.

Figure 3:
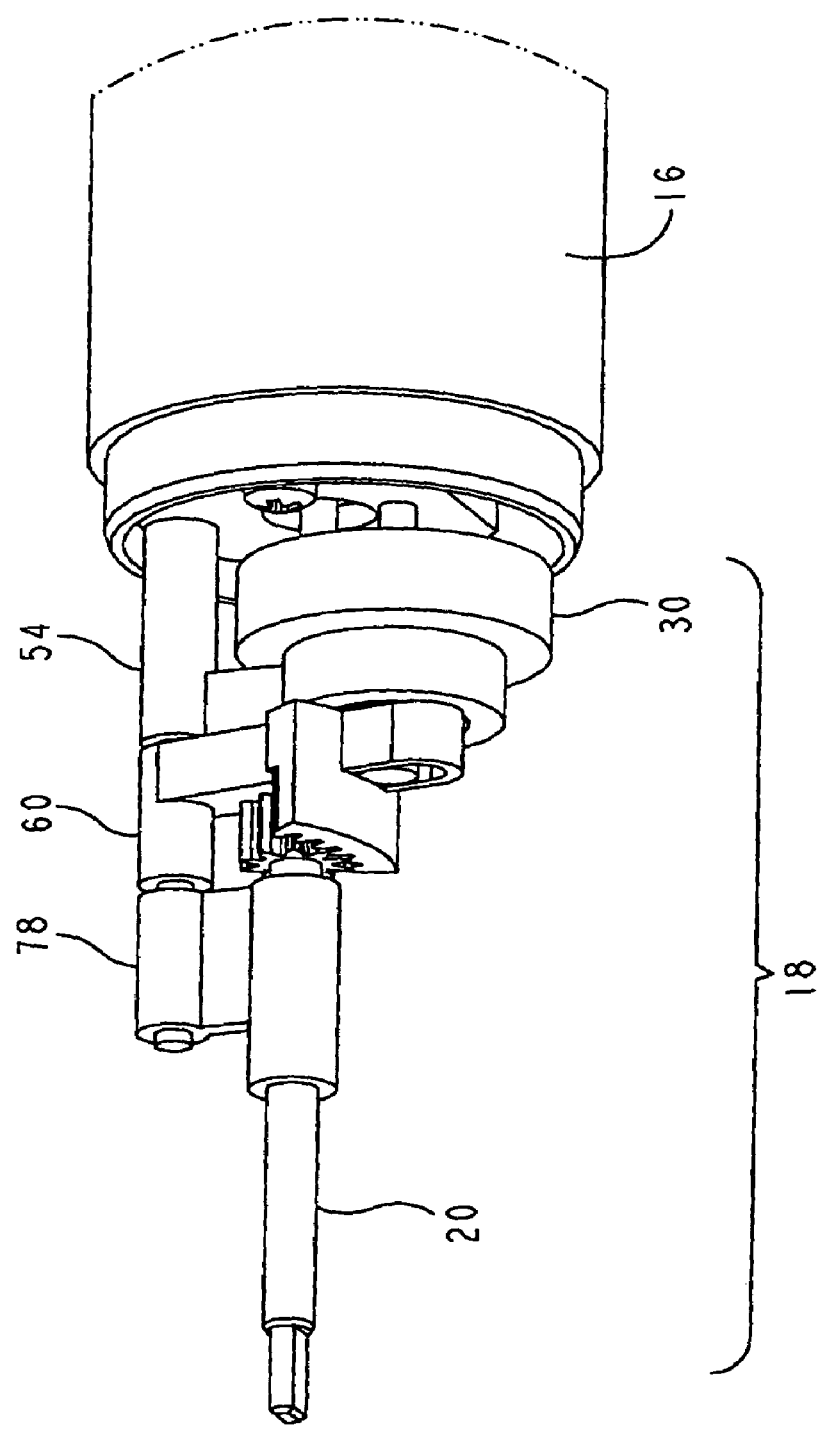
FIG. 3 is a perspective view of the portion on the electric toothbrush shown in FIG. 2.

Reference is now made to FIG. 3, which shows drive mechanism 18 assembled. It will be noted that axes 28, 34, 68 and 86 are all parallel. This is useful in that all of the components of drive mechanism 18 occupy a relatively small volume, so that they can fit in a housing that is easy to grasp and hold in a user's hand.

In an alternative embodiment transmission 102 can be any suitable means for transferring rotational motion into rotational reciprocating motion, and particularly rotational reciprocating motion about an axis parallel to that of the motor output shaft.

In an alternative embodiment, the second transmission 104 can be any suitable means for changing the angular sweep of reciprocation and the average angular speed of reciprocation.

As shown, brush head 96 can have a circular arrangement of bristles 98. Alternatively, however, the brush head can have any suitable arrangement of bristles.

As will be apparent to persons skilled in the art, various modifications and adaptations of the device described above are contemplated without departure from the present invention.

What is claimed is:

1. An electric toothbrush, comprising:
    a housing;
    an electric motor connected to said housing, said electric motor having a motor output member for rotation about a motor output axis;
    a first transmission linked to said motor output member, said first transmission to convert rotational movement from said motor output member into rotational reciprocating movement at a first average angular speed and a first average angular sweep about a first transmission output axis; and
    a second transmission linked to said first transmission, said second transmission to convert rotational reciprocating movement from said first transmission into rotational reciprocating movement at a second average angular speed and a second average angular sweep about a second transmission output axis that is parallel to said motor output axis and to drive an output member to reciprocate at said second average angular speed and said second average angular sweep about said second transmission output axis,
    and wherein, said second average angular speed is greater than said first average angular speed and said second average angular sweep is greater than the first average angular sweep.

2. The electric toothbrush as claimed in claim 1, wherein said second transmission comprises a first gear member and a second gear member, said second gear member being drivenly connected to said first gear member, said second gear member having a smaller radius than said first gear member.

3. The electric toothbrush as claimed in claim 2 wherein said said first gear member comprises a section of an internal gear connected to said first transmission, and said second gear member comprises a spur gear.

4. The electric toothbrush as claimed in claim 1, wherein said motor output member comprises a first gear, and said first transmission comprises:
    a rotatable second gear member which mates with said first gear member;
    an orbiting member attached to said second gear, to convert rotation of said second gear to orbital movement; and a rotatable slotted member slidably connected to said orbiting member, to convert said orbital movement into rotational reciprocating movement at said first average angular speed.

5. The electric toothbrush as claimed in claim 4, wherein said rotatable second gear is an internal gear.

6. The electric toothbrush as claimed in claim 1, wherein said output member comprises a brush head having an axis that is angled relative to said second transmission output axis.

* * * * *